United States Patent
Duesing (10) Patent No.: US 7,611,315 B2
(45) Date of Patent: Nov. 3, 2009

(54) MOTOR ELEMENT, IN PARTICULAR MEDICAL HANDPIECE WITH A COLLET CHUCK

(75) Inventor: Josef Duesing, Leutkirch (DE)

(73) Assignee: Kaltenbach & Voight GmbH, Biberach (DE)

( * ) Notice: Subject to any disclaimer, the term of this patent is extended or adjusted under 35 U.S.C. 154(b) by 149 days.

(21) Appl. No.: 11/399,280

(22) Filed: Apr. 6, 2006

(65) Prior Publication Data

US 2007/0114730 A1 May 24, 2007

(30) Foreign Application Priority Data

Apr. 7, 2005 (DE) .................. 10 2005 016 046
Apr. 12, 2005 (DE) .................. 10 2005 016 869

(51) Int. Cl.
*B23B 31/20* (2006.01)
(52) U.S. Cl. .................. 409/233; 279/46.7; 279/50; 433/129
(58) Field of Classification Search ............ 279/50, 279/51, 52, 16, 17, 143, 145, 43.7, 46.7, 279/43, 43.3, 43.4, 43.5, 46.1, 46.2, 46.3, 279/46.4; 408/127, 239 R; 433/112, 114, 433/127, 129; 409/233, 232; *B23B 31/20*
See application file for complete search history.

(56) References Cited

U.S. PATENT DOCUMENTS

| 382,673 | A | * | 5/1888 | Williams ............ | 279/51 |
| 2,278,267 | A | * | 3/1942 | Holmes ............ | 279/51 |
| 2,746,758 | A | * | 5/1956 | Haviland et al. ............ | 279/53 |

(Continued)

FOREIGN PATENT DOCUMENTS

DE 44 06 855 A1 9/1995

(Continued)

OTHER PUBLICATIONS

Search Report in DE 10 2005 016 869 dated Dec. 22, 2005.

(Continued)

*Primary Examiner*—Eric A Gates
(74) *Attorney, Agent, or Firm*—Marshall, Gerstein & Borun LLP (57) ABSTRACT

In the case of a motor element, in particular of dental technical handpiece or a motor spindle, which at least in its front region has an elongated shank, rotatably mounted in which there is a hollow drive shaft, arranged in whose front end region there is a collet chuck for a tool that is connected in its rear end region by means of a coupling to a rod that extends towards the rear and is pretensioned towards the rear or towards the front by means of the force of a spring and can be displaced towards the front or towards the rear against the force of the spring by means of an actuating mechanism, with the spring being stayed on the draw rod towards the rear and being stayed against an inner first shoulder of the drive shaft towards the front, arranged at the front end region of the spring there is at least one supporting element that is elastically pretensioned radially outwards and springs out behind the shoulder when the draw rod is pushed with the spring from the front into the drive shaft, and the supporting element reaches a position located behind the shoulder.

4 Claims, 8 Drawing Sheets

U.S. PATENT DOCUMENTS

| | | | | |
|---|---|---|---|---|
| 2,970,508 | A * | 2/1961 | Wicks | 86/23 |
| 3,171,664 | A * | 3/1965 | Benjamin et al. | 279/50 |
| 3,712,386 | A * | 1/1973 | Peters | 173/46 |
| 3,724,563 | A * | 4/1973 | Wickham et al. | 173/221 |
| 3,942,392 | A * | 3/1976 | Page et al. | 433/129 |
| 4,040,311 | A * | 8/1977 | Page et al. | 433/105 |
| 4,114,276 | A * | 9/1978 | Malata et al. | 433/129 |
| 4,355,977 | A * | 10/1982 | Ota et al. | 433/131 |
| 5,609,445 | A | 3/1997 | Dusing | 408/124 |
| 5,806,859 | A * | 9/1998 | Saccomanno, III | 279/143 |
| 6,090,122 | A | 7/2000 | Sjostrom et al. | 606/180 |
| 6,193,591 | B1 * | 2/2001 | Stahl et al. | 451/243 |
| 6,260,855 | B1 * | 7/2001 | Curtis | 279/51 |
| 6,402,442 | B2 * | 6/2002 | Akamatsu et al. | 409/134 |
| 6,568,889 | B2 * | 5/2003 | Rohm | 409/233 |
| 6,663,088 | B2 * | 12/2003 | Kimura | 267/64.28 |
| 6,674,189 | B2 * | 1/2004 | Watanabe et al. | 310/52 |
| 7,137,632 | B2 * | 11/2006 | Smith | 279/4.08 |
| 7,287,941 | B1 * | 10/2007 | Erickson | 409/233 |
| 7,393,311 | B1 * | 7/2008 | Giovanelli et al. | 483/1 |
| 2002/0014141 | A1 * | 2/2002 | Prust et al. | 82/147 |

FOREIGN PATENT DOCUMENTS

| | | |
|---|---|---|
| DE | 202004005966 | 7/2004 |
| JP | 07255745 A * | 10/1995 |
| JP | 07255746 A * | 10/1995 |

OTHER PUBLICATIONS

European Search Report in DE 02005016035 dated Dec. 22, 2005.

* cited by examiner

MOTOR ELEMENT, IN PARTICULAR MEDICAL HANDPIECE WITH A COLLET CHUCK

BACKGROUND OF THE INVENTION

1. Field of the Invention

The invention relates in particular to a medical handpiece.

2. Description of Related Technology

A handpiece of this kind is described in DE 44 06 855 A1. In the case of this previously known handpiece, a collet chuck is arranged in the front end region of a hollow drive shaft and is connected on the rear side to a draw rod, for the compression of the collet chuck, which at the same time is a longitudinal section of the drive shaft. The draw rod is formed by a pressure spring that is arranged between it and the hollow drive shaft in the form of a helical spring that is stayed with its front end at a shoulder of the hollow drive shaft directed towards the rear and acts with its rear end on a shoulder of the draw rod directed towards the front and thus pretensions the draw rod towards the rear. In this connection, the drive shaft in the region of the pressure spring consists of two sleeve-shaped portions that are extended in terms of their cross-sectional size with regard to the other axial sections of the drive shaft and overlap each other and are fixedly connected together. In the case of this known development, a complicated construction emerges that not only results in large cross-sectional dimensions, but also presupposes expensive assembly and disassembly.

GENERAL DESCRIPTION OF THE INVENTION

The underlying object of the invention is to develop a medical handpiece of the kind specified at the beginning in such a way that, whilst guaranteeing a simple construction, assembly and disassembly can be effected with little outlay.

In the case of the handpiece in accordance with the invention, arranged at the front end of the spring there is at least one supporting element that is elastically pretensioned outwards and springs out behind the shoulder when the rod is pushed with the spring from the front into the drive shaft, and the supporting element reaches a position located behind the shoulder. As a result, not only is it possible to achieve a construction that has a small cross-sectional size, but assembly of the rod with the spring is also possible from the front, this resulting in a substantial simplification, because the handpiece does not need to be opened at the rear for the assembly and subsequently be closed again. The construction of small cross section that is striven for is therefore possible, because already a slight engagement behind the shoulder by the supporting element renders possible reliable staying of the spring towards the front, and the handpiece can therefore be realized with a small cross-sectional size.

The supporting element can be formed in a simple and inexpensive manner by means of a spring arm that can be sprung out of a relaxed position, in which it engages behind the shoulder, radially inwards into a position in which it is adapted to the inner cross-sectional size of the drive shaft.

The introduction of the supporting element into the drive shaft can be simplified and configured in a handling-friendly manner thereby if arranged on the rear side on the supporting element and/or on the front edge of the drive shaft there is an oblique or rounded lead-in face which when pushing in the rod with the spring automatically causes the supporting element to spring into the position in which it fits in the receiving hole of the drive shaft.

The shoulder in the drive shaft can be formed by an annular groove. It is not only possible to produce such a development simply and inexpensively, but when pushing in the rod with the spring there is no need to pay heed to any particular rotational position, because the supporting element matches the shoulder face in each rotational position.

A further advantage of the development in accordance with the invention lies in the fact that the rod with the spring can be disassembled by pushing it further from the front towards the rear, for which purpose, if applicable, the handpiece can be opened at the rear so that the rod with the spring can be pushed out towards the rear. If in this connection oblique or rounded lead-in faces are provided for the supporting element at the rear on the supporting element or on the rear edge of the annular groove, these automatically give rise to a springing-in of the supporting element.

The development in accordance with the invention also renders possible in this respect a simple construction that can be produced inexpensively, because the receiving hole in the drive shaft can be formed so that it is hollowly cylindrical substantially over the whole of its length.

Within the scope of the invention it is possible to provide one or more supporting elements that are arranged so that they are distributed over the periphery. In this connection, it is advantageous to form the supporting element or elements on a guide ring or on a guide bushing in which the draw rod can be guided in a sliding manner.

Further developments of the invention, whilst guaranteeing simple developments, improve the advance or backward movement of the rod for the purpose of opening or closing the collet chuck by means of a pressure element, which is manually accessible from outside the handpiece, and return by spring force.

The present invention is not restricted to medical or dental applications but can generally be used with motor elements with a collet chuck for a rotatable tool. Another application would—for example—be a high frequency motor spindle.

BRIEF DESCRIPTION OF THE DRAWINGS

Advantageous developments of the invention are explained in greater detail in the following with the aid of an exemplary embodiment and drawings, in which.

DETAILED DESCRIPTION OF THE INVENTION

In the following, a preferred embodiment of the present invention is described be means of a medical handpiece (hereinafter "handpiece") for a medical or dental laboratory. It has to be emphasized, however, that the solution according to the present invention can also be used in other motor elements, for example in spindle systems.

Figure 1:
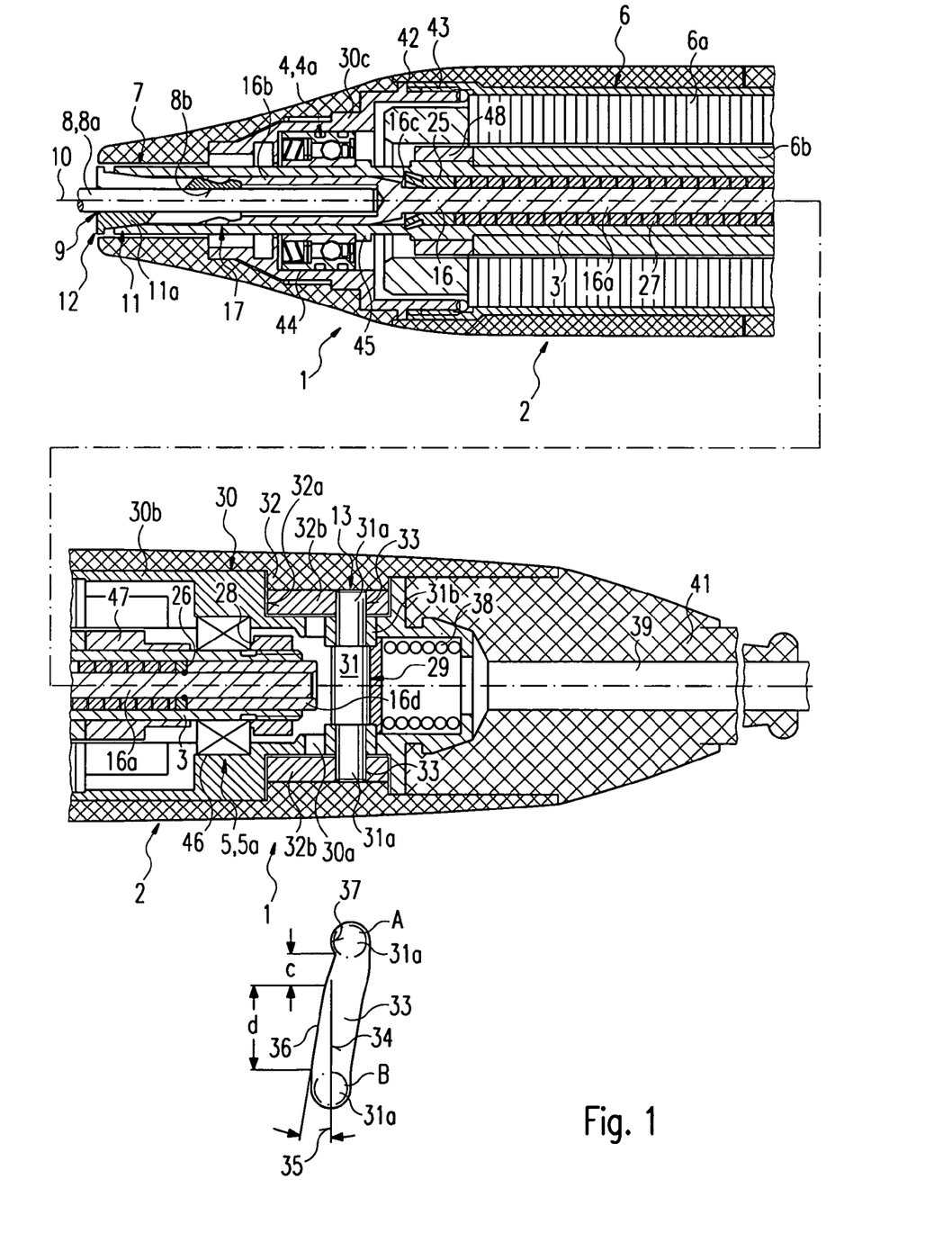
FIG. 1 shows a medical handpiece in accordance with the invention in an axial longitudinal section.

The handpiece 1 is on account of its stable and sufficiently large construction suitable for machining casts, artificial parts such as prostheses, or impressions of the human or animal body. In technical terminology the handpiece 1 is termed a medical technical or dental technical handpiece or working handpiece. The exemplary embodiment is less well suited for treating teeth in the mouth space of a patient because of its construction size. However, the invention realized in the case of the exemplary embodiment is in principle also suitable for such handpieces that are suitable for the treatment of teeth in the mouth space of a patient. The same also applies to the medical field.

The main portions of the handpiece 1 are a shank 2 which is used for manual gripping and extends in a straight manner at least in its front region and in the case of the exemplary embodiment extends so that it is straight as a whole, a drive shaft 3 which extends longitudinally in the shank 2 and is mounted in the shank 2 so that it is rotatable in a front and a rear pivot bearing 4, 5 and is axially non-displaceable, a drive motor 6 which is preferably electric and is arranged in the shank 2 as a rotary drive for the drive shaft 3, and a clamping arrangement 7 for a tool 8, shown by way of indication, which can be plugged with a tool shank 8a into a plug hole 9 of the clamping arrangement 7 and can be clamped and can also be disconnected again.

The clamping arrangement 7 has a tool-holder 12 which is preferably formed by a so-called collet chuck 11 which in the case of the exemplary embodiment is mounted in the drive shaft 3 so that it can be displaced in its longitudinal direction and has a plurality of, for example three, clamping segments 11a which are arranged on the end side and so that they are distributed over the periphery and can be clamped by means of a clamping mechanism against the tool 8 or the tool shank 8a and can also be released again by means of a release mechanism 13 that is manually accessible from without. The collet chuck 11 can be longitudinally displaced between a clamping position and a position of release for the clamping and releasing process. In the case of the exemplary embodiment, the clamping segments 11a are preferably compressed radially inwards against the tool 8 or its shank 8a when the collet chuck 11 moves back. A clamping cone 15 with an inner cone 15a in the drive shaft 3 and matching outer cone faces 15b on the clamping segments 11a is used for this purpose. In the position of release of the collet chuck 11 where it is displaced towards the front, the clamping segments 11a are not under any clamping pressure so the tool shank 8a can be plugged into or drawn out of the collet chuck 11. So that the clamping segments 11a are not moved too far radially inwards in the absence of the tool 8, arranged at the front ends of the clamping segments 11a there are flange pieces 11b that limit the movement of the collet chuck 8 axially inwards by butting against the drive shaft 3.

A longitudinally extending rod 16, in the exemplary embodiment in accordance with FIG. 1, a draw rod that is mounted so that it is coaxially displaceable in the drive shaft 3 and is detachably connected at its front end to the rear end of the collet chuck 11, is used to move the collet chuck 11 to and fro in a longitudinally directed manner. To this end, arranged between the rod 16 and the collet chuck 11 there is a coupling 17, which is effective axially and in a form-locking manner, having a first coupling element 17a on the one portion that is to be coupled and a second coupling element 17b on the other portion that is to be coupled, with the first coupling element 17a being moveable between a coupling position where it engages in a form-locking manner behind the other coupling element 17b in an undercut 17c and a position of release where it has moved out of the undercut 17c and being capable of being locked by means of a locking element 8b in the coupling position. As a result of the locking it is guaranteed that the movable coupling element 17a not only engages behind the other coupling element 17b in the coupling position in a form-locking manner, but that it is also locked therein in order to prevent it from moving out As a result, the coupling security is guaranteed so that the coupling 17 can transmit axial forces from the rod 16 to the collet chuck 11 or vice-versa.

The invention is not limited to a tool-holder 12 in the form of a collet chuck 11. Within the scope of the invention a clamping arrangement 7 can be provided, for example, in the front end region of the tool-holder 12 and have, for example, a gripping screw with which a tool can be firmly gripped on the tool-holder. That is why the description continues in the following with reference to the component tool-holder 12, if a collet chuck 11 is not required.

Within the scope of the invention, the radially movable first coupling element 17a can be arranged on the rod 16 and the radially rigid second coupling element 17b can be arranged on the tool-holder 12. In the case of the exemplary embodiment, the reverse arrangement is provided. The first coupling element 17a is arranged on the tool-holder 12 and the second coupling element 17b is arranged on the rod 16. Such a tool-holder 12 has a rear tool-holder section with which it can be plugged into the drive shaft 3, formed so that it is hollow in the front-end region, as far as the region of the coupling 17. A spring element which pretensions the first coupling element 17a into its coupling position where it engages behind preferably automatically effects the movement of the first coupling element 17a into the undercut 17c. In the case of the exemplary embodiment, the first coupling element 17a is arranged on a spring arm 19, which extends towards the rear from the tool-holder body, and protrudes radially outwards from this spring arm 19. The first coupling element 17a and the spring arm 19 are separated from the rest of the body of the tool-holder 12 by means of radial longitudinal slots 21 that open out axially at the associated end.

Figure 5:
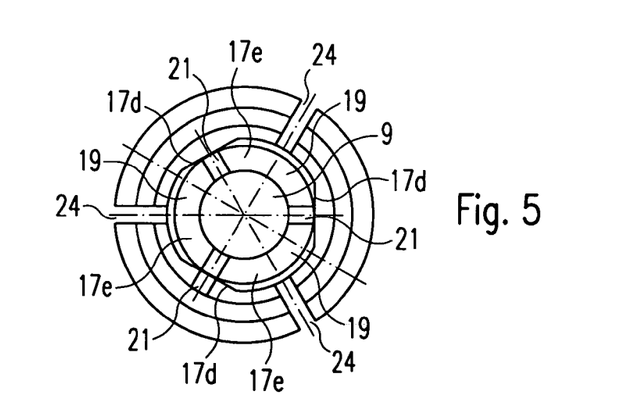
FIG. 5 shows the collet chuck of FIG. 3 in a plan view.

It is advantageous, in order to achieve rotational securement, to form the undercut 17c, which in the case of the exemplary embodiment is provided behind the second coupling element 17b, namely the counter-coupling element, with recessed faces 17d that delimit the first coupling element 17a in both peripheral directions with clearance of motion (FIG. 5). In this respect, rotational securement that is effective in both peripheral directions in a form-locking manner results for the tool-holder 12 in the drive shaft 3. It is, however, also advantageous to form the undercut 17c as an annular groove or as a groove that continues in the clamping segments 11a in the peripheral direction. In such a case, whilst there is no rotational securement in the region of the coupling 17, the advantage that is achieved as a result is that the tool-holder 12 can be pushed into the coupling 17 in any selectable rotational position and can be coupled. Rotational securement can then be realized in a different way. In the case of the formation of the tool-holder 12 as a collet chuck 11, rotational securement is provided by the gripping cone of the collet chuck 11.

In order to facilitate the assembly and/or disassembly of the tool-holder 12, it is advantageous to form the first coupling element 17a and/or the second coupling element 17b with front or rear oblique or rounded lead-in faces 22a, 22b or lead-out faces 23a, 23b respectively which have such a great incline with regard to the longitudinal central axis and rotational axis 10 of the drive shaft 3 that the tool-holder 12 can be pushed into the coupling 17 and/or drawn out of the coupling 17 with an axial force that can be applied in a handling-friendly manner, with the movable coupling element 17a springing out automatically. As a result, a latching arrangement is formed whose latching faces are so large that during the functional operation the axial coupling of the tool-holder 12 is guaranteed and the coupling 17 can be over-pressed, for assembly and/or disassembly of the tool-holder 12, with axial expenditure of force that can be applied manually.

In the case of the exemplary embodiment, in which a plurality of, preferably three, movable first coupling elements 17a with associated second coupling elements 17b with undercuts 17c are arranged so that they are distributed over the periphery, the movable coupling elements 17a are formed with the associated spring arms 19 in each case as identical segments that are arranged on the end side and are separated from each other by means of preferably three longitudinal slots 21 that open out on the end side. The width of the longitudinal slots 21 that is directed in the peripheral direction is so great that the movable coupling elements 17a can spring out in each case, with the existing width of the longitudinal slots 21 thereby being reduced somewhat in each case.

Figure 3:
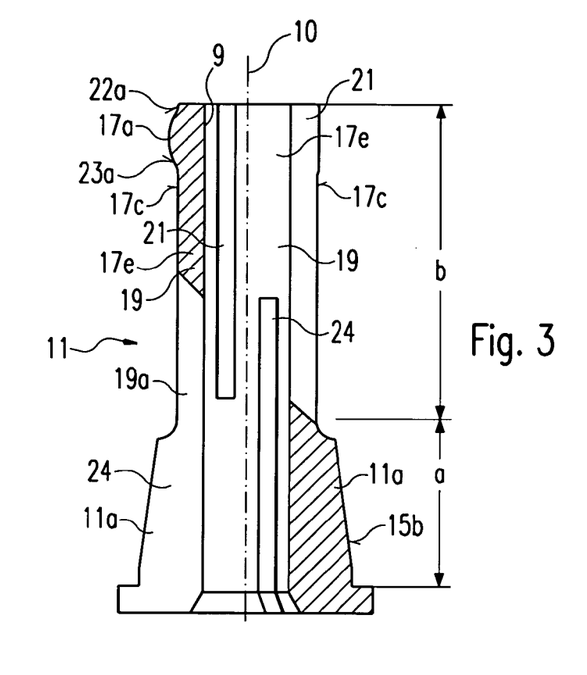
FIG. 3 shows a collet chuck of the handpiece in an axial section.
Figure 4:
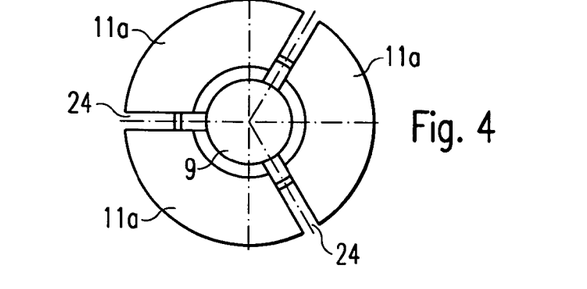
FIG. 4 shows the collet chuck of FIG. 3 in a view from below.

When the tool-holder 12 is formed as a collet chuck 11 with a plurality of, preferably three, clamping segments 11a, which are arranged so that they are distributed over the periphery, are separated from each other by means of longitudinal slots 24 and are arranged on spring arms 19a formed thereby, in order to reduce the overall length it is advantageous to arrange the longitudinal slots 21 in relation to each other so that they are staggered with regard to the longitudinal slots 24 in the peripheral direction, with it being possible for the longitudinal slots 21, 24 to overlap each other, as clearly shown in FIG. 3.

The sleeve-shaped tool-holder 12 has a hollowly cylindrical plug hole 9, a front conical longitudinal section a and a substantially hollowly cylindrical longitudinal section b extending from the latter towards the rear, the longitudinal sections each being formed by the previously described segments. The cross-sectional shape and size of the plug hole 9 is adapted with little clearance of motion to the cross-sectional shape and size of the tool 8 or tool shank 8a respectively. The wall sections of the preferably hollowly cylindrical plug hole 9 thus form in the region of the clamping segments 11a hollow-cylinder-section-shaped clamping faces and in the region of the coupling segments hollow-cylinder-section-shaped stop faces, with which the coupling segments 17e rest against the peripheral face of the tool 8 or shank 8a respectively.

Figure 2:
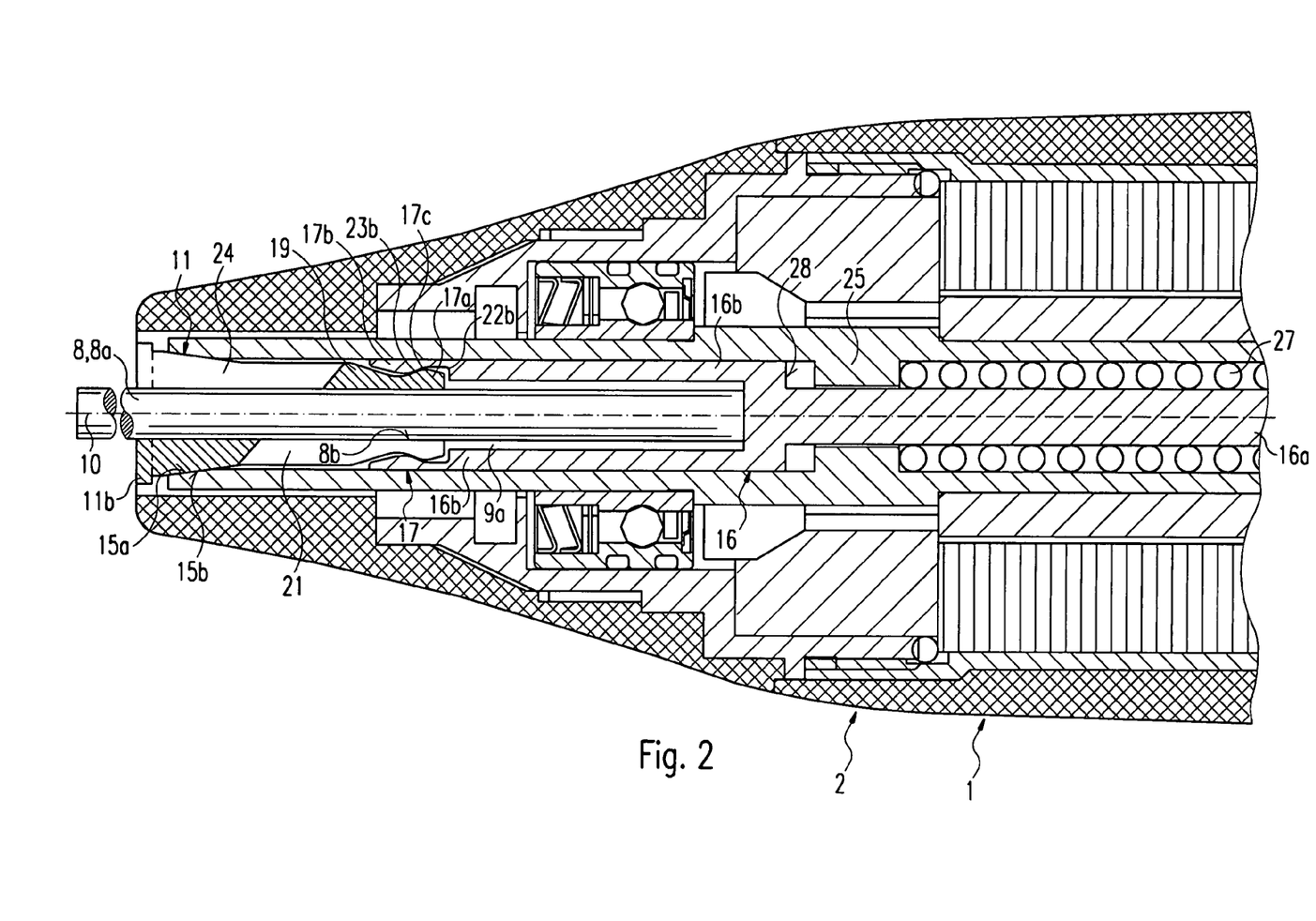
FIG. 2 shows the front end region of the hand piece in a modified, enlarged representation.

The developments in accordance with FIG. 1 or 2 respectively, on the one hand, and FIG. 5, on the other hand, differ as a result of the lateral surface form of the coupling elements 17e. In accordance with FIG. 1 or 2, the coupling elements 17e are thicker before the associated undercut 17c, with the undercuts 17c being concavely rounded in the longitudinal cross section. In accordance with FIG. 5, the undercut 17c extends from the convex coupling elements 17a substantially cylindrically towards the front.

In the case of the exemplary embodiment, the rod 16 extends from the coupling 17 towards the rear longitudinally through the sleeve-shaped drive shaft 3, preferably projecting thereby over the rear end of the drive shaft 3. Behind the front end region of the rod 16, in which a plug hole 9a is arranged, the rod 16 extends with a rod section 16a that tapers in cross section and is guided in a longitudinally displaceable manner in its front end region in a guide bushing 25 in the drive shaft 3. Located between the rear end of the guide bushing 25 and a shoulder face 26 that is directed towards the front in the rear end region of the rod 16 there is a pressure spring 27 in the form of a helical spring on the tapered rod section 16a pre-tensioning the rod 16 towards the rear. When the tool-holder 11 is disassembled, the thickened front end region 16b of the rod 16 rests with a rear-side shoulder face 16c against the guide bushing 25. The shoulder face 26 that is arranged on the rear side thereof can be formed by a bushing 16d that is pushed onto the rod section 16a and is fixed thereon and with which the rear end region of the rod 16 is mounted in the sleeve-shaped drive shaft 3 in an axially displaceable manner. The guide bushing 25 in FIG. 2 differs from the other exemplary embodiments in so far as it is formed by an inner ring projection of the drive shaft 3.

In the normal position, the rod 16 which is pretensioned towards the rear by the spring 27 is limited in its movement directed towards the rear in that when a tool 8 is plugged into the collet chuck 11 the outer cone of the collet chuck 11 rests against the inner cone of the drive shaft 3. In order to release the tool 8, the rod 16 is moved forwards by the actuating mechanism 13. This can be effected by means of a pressure element 29 which is formed, for example, as a preferably cylindrical cross pin 31 which can be moved forwards towards the rear end of the rod 16 (portion 16a and/or 16d) by means of the actuating mechanism 13. In the case of the exemplary embodiment, the cross pin 31 is displaceably mounted in the region of its, for example, tapered ends 31a in grooves 33 which are located with a pitch in the peripheral direction of the handpiece 1 in an actuating sleeve 32 which is mounted in an annular groove 32a of the handpiece 1 so that it cannot be displaced axially and so that it is rotatable in the peripheral direction. One of the two grooves 33 is shown by way of example in FIG. 1 as a developed view. The grooves 33, which are preferably arranged in an inner bushing 32b, made in particular from wear-resistant material, for example steel, extend in the peripheral direction in such an oblique or rounded manner that starting from the clamping position shown in FIG. 1 given a relative twist of the actuating sleeve 32 the pressure element 29 is displaced towards the front and thereby moves the rod 16 towards the front and releases the collet chuck 11. In this position of release, the ends 31a of the pressure element 29 are located in the end regions B of the grooves 33. In this connection, the arrangement can be such that the end region B of the grooves 33 that is associated with the position of release is not directed obliquely, but in the peripheral direction so that any automatic untwisting of the actuating sleeve 32 on account of the spring tension and, if applicable, on account of the effect of vibrations is prevented. The incline 36 running obliquely towards the front with regard to an associated transverse plane 35 that is directed at right angles to the longitudinal central axis can vary in the region of the length of the grooves 33. In the case of the exemplary embodiment, starting from the end region A that is associated with the clamping position, a comparatively greatly inclined course of inclination c is provided, following which there is a course of inclination d that is inclined less greatly, following which there is an end region B of the grooves 33 that is directed in the peripheral direction. Provided in the end regions B of the grooves 33, in which the pressure element ends 31a are located in a position that corresponds to the clamping position, there are preferably locating depressions 37 in which the ends 31a can latch and which are directed towards the front in the case of the exemplary embodiment. The pressure element 29 can be pretensioned towards the front and thus also into the locating depressions 37 by means of a spring 38, for example a helical pressure spring, that is arranged behind the pressure element 29. When the actuating sleeve 32 is rotated into the position of release B, the pressure element 29, the rod 16 and the collet chuck 11 are moved forwards into the position of release. When the actuating sleeve 32 is turned back into the clamping position A, the pressure element 29 is moved back again into the distanced clamping position (free position) in which it frees the rod 16, and the collet chuck 11 is clamped on account of the axial spring force that exists.

In the case of the previously described forward and backward movements of the pressure element 29, said element is guided longitudinally, for example by means of sliding sleeves 31b that sit thereon, in longitudinal grooves 30a of a bearing peripheral wall 30b of a handpiece housing 30.

The electric motor 6 is provided as a rotary drive for the drive shaft 3, this being arranged in the handpiece 1 and being arranged, for example, with a sleeve-shaped stator 6a on the inside of the peripheral wall of the existing handpiece housing and sitting with its sleeve-shaped rotor 6b on the drive shaft 3. An electric current line 39, which is shown by way of indication, extends from the rear through a flexible cable bushing 41 made from elastically deformable material which is connected to a rear housing section of the handpiece housing.

The housing 30 includes two bearing peripheral walls, namely the rear longer peripheral wall 30b and a front shorter peripheral wall 30c that overlap in the front region of the housing 30 and in this region are screwed together by means of an outside thread and an inside thread set therein and adjoin each other at a division joint 42. The screw connection that is arranged, for example, behind the division joint 42 is denoted by 43. The rear peripheral wall 30b is formed so that it is substantially hollowly cylindrical and the stator 6a is arranged in the region thereof. The front handpiece section and the front peripheral wall 30c taper towards the front end of the handpiece 1.

The front pivot bearing 4 is arranged in the front peripheral wall 30c and is formed by a rolling bearing 4a which on the outside sits in a bearing bore 44 that is open towards the rear in the front peripheral wall 30c and on the inside sits on the hollow drive shaft 3, being delimited on the rear side by an annular collar 45 on the drive shaft 3.

The rear pivot bearing 5 is also formed by a rolling bearing which on the outside sits in a bearing bore 46 that is open towards the front in the rear end region of the rear peripheral wall 30b and on the inside sits on the drive shaft 3. The inner ring of the rear rolling bearing 5a is delimited on its front side by the rotor 6b or an intermediate sleeve 47 that rests therein. The rotor 6b is delimited at its front end by an annular collar 48 on the drive shaft 3 which could also be formed by the annular collar 45. Located on the rear side of the rear rolling bearing 5a there is a threaded nut 49 which is screwed from the rear onto a threaded section of the drive shaft 3 and presses the inner ring and also the further ring portions that are arranged on the front side of the latter on the drive shaft 3 against the annular collar 48 and axially fixes them.

Figures 6, 7:
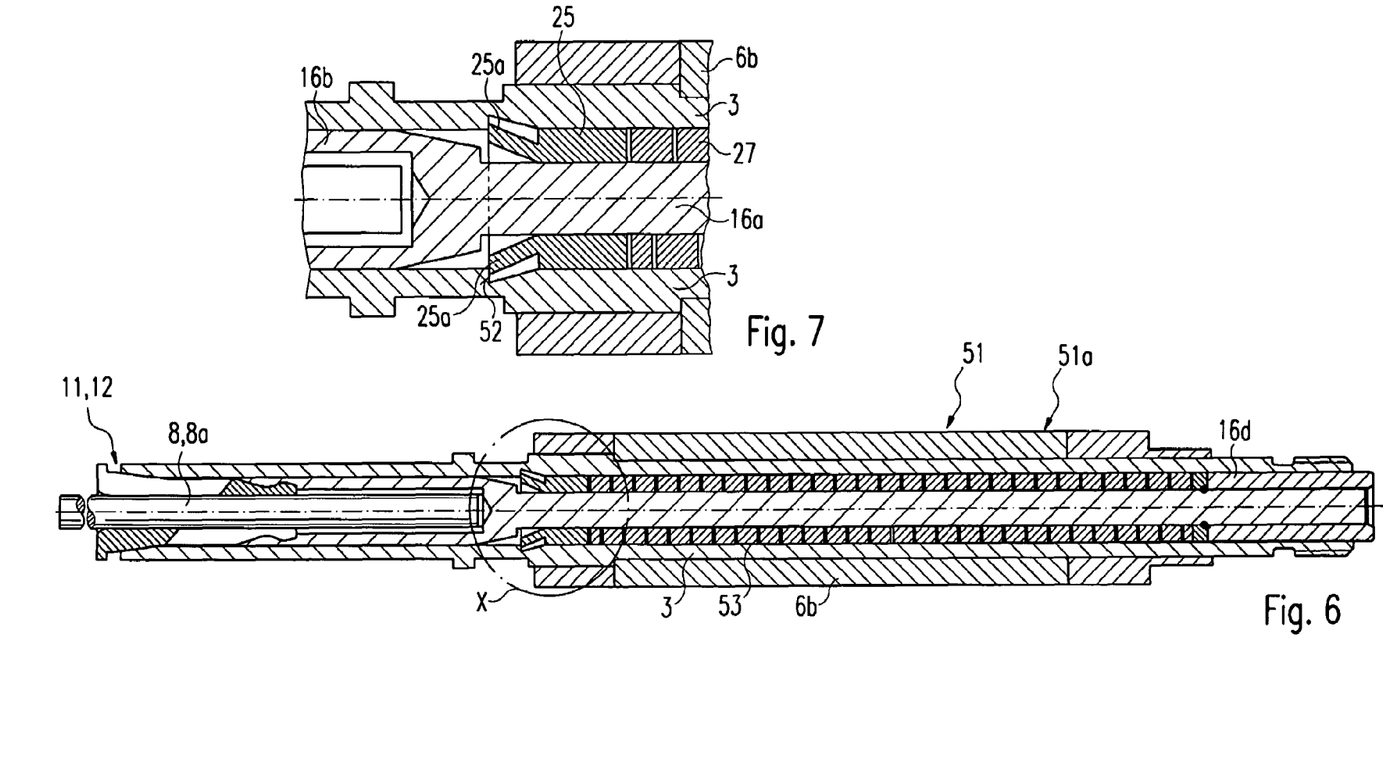
FIG. 6 shows a drive shaft constructional unit in an axial longitudinal section.
FIG. 7 shows the drive shaft constructional unit of FIG. 6 in the detail marked by X in an enlarged sectional representation.
Figure 8:
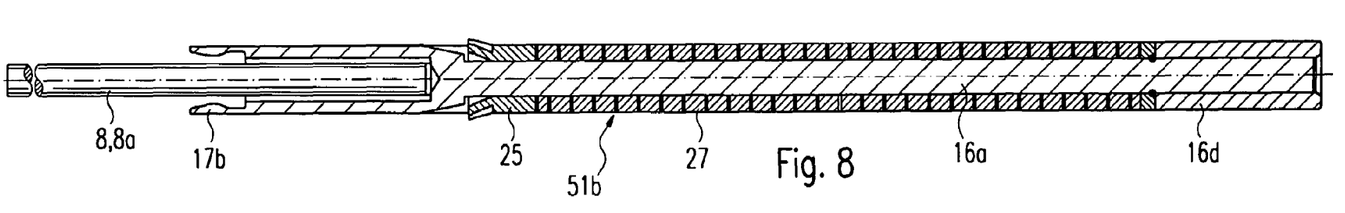
FIG. 8 shows a draw-rod constructional unit in an axial section.

In this connection, the drive shaft 3 with the rotor 6b and the rod 16 with the pressure spring 27 form a constructional unit 51 that can be preassembled, see FIG. 6.

In the case of the present exemplary embodiment, this constructional unit 51 includes two constructional units 51a, 51b, with the constructional unit 51a having the drive shaft 3, the rotor 6b, whilst the second constructional unit 51b has the rod 16, the bushing 16d, the pressure spring 27 and the guide bushing 25.

One or more shoulder faces 52 that are directed towards the rear and against which the guide bushing 25 is limited in the direction towards the front and positioned are provided in the drive shaft 3 behind the thickened end region 16b for the axial positioning of this constructional unit 51b. The pressure spring 27 is stayed on the rear side on the bushing 16d and it pretensions the guide bushing 25 towards the front, pretensioning the rod 16 towards the rear on account of the axial staying of the guide bushing 25 on the at least one shoulder face 52. In the assembled state, in this case the rod 16 or the bushing 16d is stayed on the rear side on the pressure element 29. This staying can, however, also be effected by delimiting the collet chuck, the clamping segments 11a or the flange pieces 11b on the rear side by means of the drive shaft 3.

In the case of the present exemplary embodiment, the inner constructional unit 51b can be plugged from the front into the hollow drive shaft 3 and be assembled. This is achieved in that the guide bushing 25 has at its front end one or more spring arms 25a which are arranged so that they are distributed over the periphery and the front ends of which in the relaxed state take up a radial measure with regard to the longitudinal central axis 10 that is greater than the radial measure of the receiving hole 53, which is cylindrical preferably over the whole of its length, in the drive shaft. The shoulder face 52 is formed by an annular groove in the receiving hole 53.

In order to install the inner constructional unit 51b in the drive shaft 3, the constructional unit 51b is plugged from the front into the receiving hole 53 until the spring arm or arms 25a, which thereby spring therein, spring out behind the at least one shoulder face 52 and position the constructional unit 51a towards the front at the at least one shoulder face 52.

In the disassembled state, on account of the spring tension of the pressure spring 27 the guide bushing 25 rests against the shoulder face 16c that is arranged in front of it. In the assembled state, on the other hand, between the shoulder face 16c and the guide bushing 25 there is axial clearance of motion even in the clamped state of the clamping segments 11a, that is, in the state in which they have been displaced towards the rear, so the clamping effect of the clamping segments 11a that is directed radially inwards is not impaired.

In order to disassemble the constructional unit 51b, after the tool-holder 9 or the clamping segments 11a has/have been removed, the rod 16 is pushed out towards the rear, with the spring arms 25a springing in without being damaged.

Figure 9:
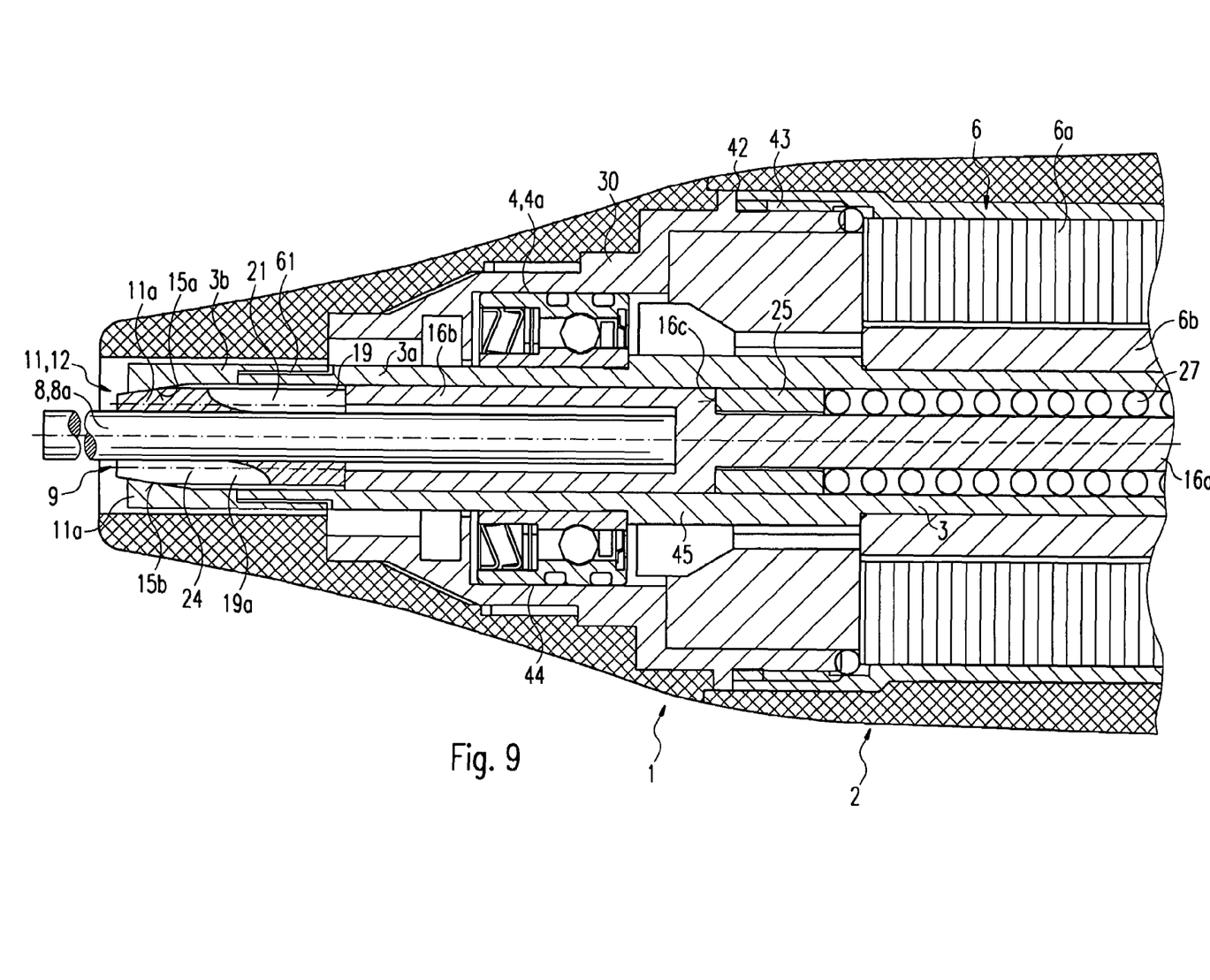
FIG. 9 shows the front end region of the handpiece in a further modified development in an axial longitudinal section.

In the case of the exemplary embodiment in accordance with FIG. 9, in which the same or comparable portions are provided with the same reference numerals, the handpiece 3 has a tool-holder 12 which is formed by a push-out collet chuck 11 that is actuated in that for a clamping process the rod 16 is not drawn back, but is pushed forward and exerts a forwardly directed pressure on the collet chuck. In the case of this development as well, a group of clamping elements formed, for example, by clamping segments 11a with cooperating cone faces are arranged in the tool-holder 12 so that they are distributed around the plug hole 9 and can be moved for a clamping process towards the plug hole 9, although the cone faces, here the inner cone 15a in the drive shaft 3 and the outer cone faces 15b on the clamping segments 11a, are formed so that they converge towards the front and in such a way that they match each other. These cone portions are preferably arranged in the front region of the collet chuck 11.

In the case of this development, no coupling between the collet chuck 11 and the rod 16 is required, since a drawing action does not take place when clamping. The pressure of the rod 16, pressing, for example, obtusely from the rear against the collet chuck 11, in which case no coupling is required, suffices for the clamping function. The collet chuck 11 is held as well in a form-locking manner so that it is undetachable between the inner cone 15a and the rod 16. In the case of this development as well, the clamping segments 11a are arranged on spring arms 19a which are formed by longitudinal slots 24 that are arranged so that they are distributed over the periphery and open out towards the front. In this connection, longitudinal slots 21 which open out towards the rear can also be provided here, subdividing the collet-chuck body into segments at the rear.

In order to facilitate the assembly of the collet chuck 11, the drive shaft 3, which is formed in a sleeve-shaped manner in this region, is transversely divided behind the inner cone 15a, and the drive-shaft portions 3a, 3b are connected together by means of a releasable connection 61, in particular a screw connection.

In the case of this modified development, the rod 16 is pretensioned by the pressure spring 27 towards the front into its clamping position. The collet chuck 11 is released by a drawing movement of the rod 16 towards the rear that can be generated by the release mechanism 13 moving it towards the rear in opposition to the force of the pressure spring 27.

For this, for example, the grooves 33 can have an opposite pitch so the pressure element 29 is moved towards the rear for the release and draws the rod 16 towards the rear, for example in that the rod 16 engages behind the pressure element 29 and thereby passes through to engage in a hole and engages behind a head portion 16e so that the spring 27 pushes the clamping elements towards the front through the rod 16 and clamps them. In this respect, the push-out collet chuck 11 is effective in an opposite way to that of the draw-in collet chuck 11 in accordance with FIG. 1.

Figure 10:
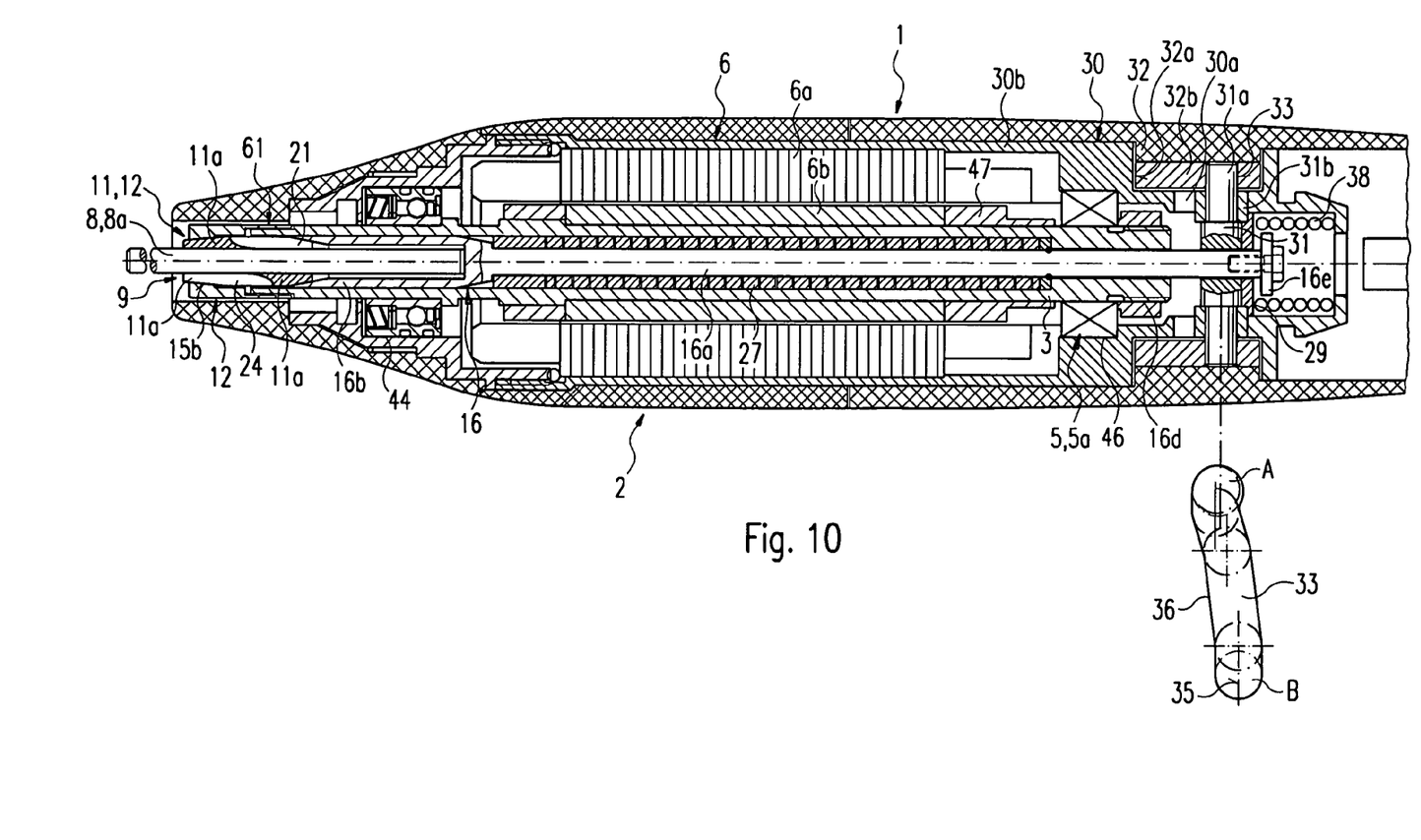
FIG. 10 shows an alternate embodiment of a handpiece in an axial longitudinal section.

The clamping effect of this tool-holder 12 can be improved in that in accordance with the exemplary embodiment in accordance with FIG. 10 two groups of clamping elements are provided that are arranged axially one after the other and in each case around the plug hole 9 and can be moved towards the plug hole 9. This can be achieved by means of common application of pressure to the groups, that is, in particular in a simple way if arranged in each group there are clamping segments of which the clamping segments 11a of the front group have outer cone faces 15b converging towards the front and those of the rear group have outer cone faces 15b converging towards the rear, with the rod 16 having at its front end a common pressure element which is formed in particular by an inner cone 15c and cooperates with the rear outer cone faces 15b. In this connection, the pressure of the rod 16 acts simultaneously on all the clamping elements.

Figure 11:
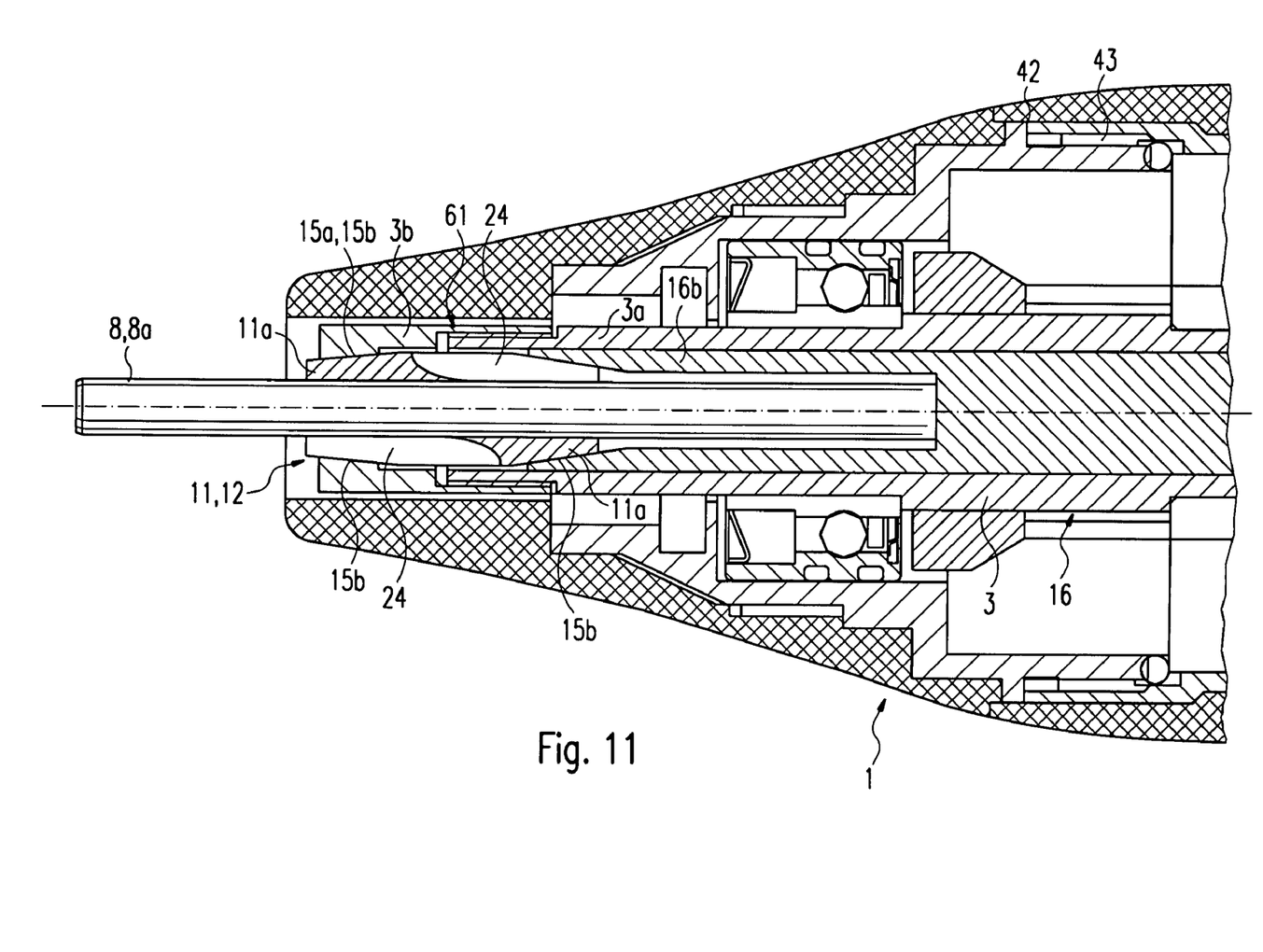
FIG. 11 shows the front end region of the handpiece in accordance with FIG. 10 in an enlarged representation.
Figure 12:
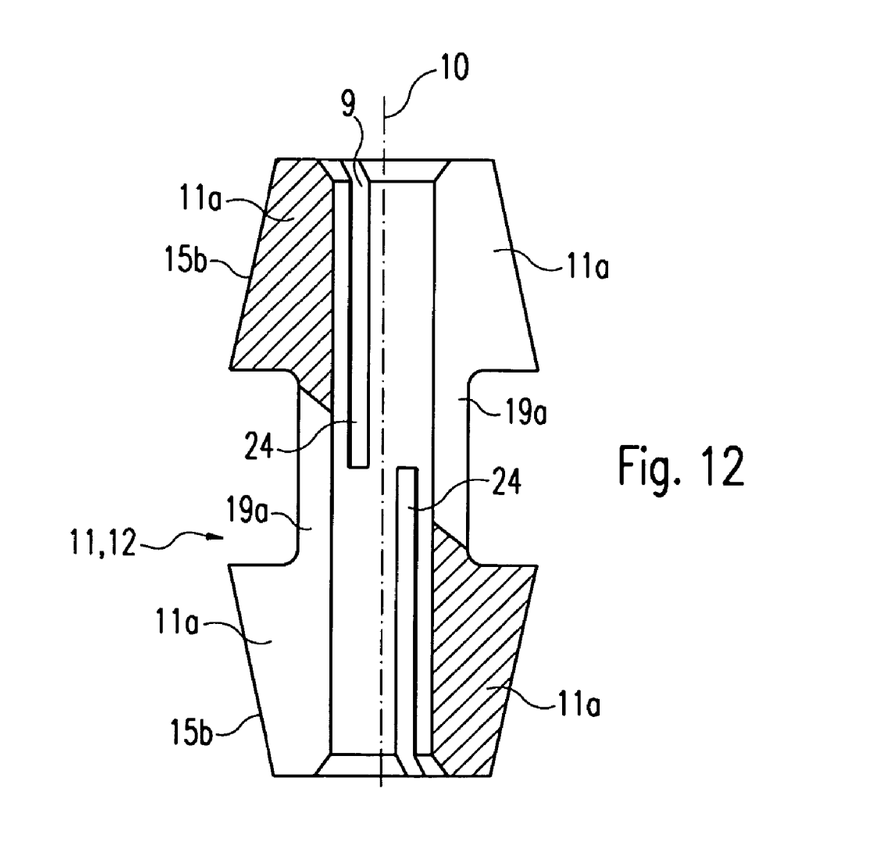
FIG. 12 shows a tool-holder in the form of a collet chuck of the handpiece in accordance with FIGS. 10 and 11 in an enlarged representation.
Figure 13:
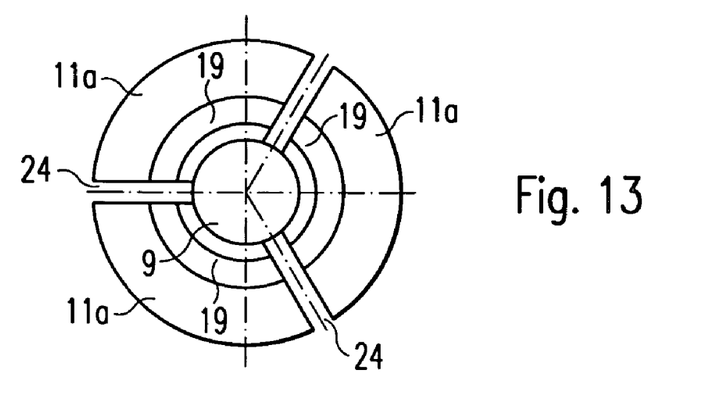
FIG. 13 shows the collet chuck in accordance with FIG. 12 in a view from below.

As FIGS. 11 and 12, show in particular, in the case of this tool-holder 12 held at both axial ends there is a respective group of, for example, three clamping segments 11a, in each case held on a spring arm 19a and thus capable of moving radially inwards against the spring-arm force. The clamping segments 11a and the spring arms 19a are formed by longitudinal slots 24 in the sleeve body that open out in each case on the end side and therefore guarantee the radial spring path. The longitudinal slots 24 and the clamping segments 11a are preferably arranged so that they are staggered in relation to each other in the peripheral direction. As a result, it is possible to arrange the slots 24 so that they overlap axially, in particular in the central region of the sleeve body and thus in the region between the groups of the clamping segments 11a or clamping elements.

As already mentioned earlier, the construction according to the present invention generally results in improvements in case a tool holder for a rotatable tool is coupled to a rod. Thus, in addition to the described medical application, the present invention can also be used in other motor driven elements, for example in a motor spindle.

The invention claimed is:

1. A motor element comprising:
   an elongated shank;
   a hollow drive shaft rotatably mounted in the elongated shank;
   a collet chuck for a tool arranged in a front end region of the hollow drive shaft; and
   a coupling that connects the collet chuck to a rod that extends rearwardly, wherein the rod is pretensioned rearwardly or frontwardly by a spring on the rod and can be displaced frontwardly or rearwardly against the spring by an actuating mechanism, the spring being rearwardly stayed on the rod and being frontwardly stayed behind an inner first shoulder of the drive shaft,
   wherein one or more spring arms are arranged at a front end region of the spring, the one or more spring arms are elastically pretensioned radially outwards and spring out behind the inner first shoulder when the rod and spring are plugged into a receiving hole of the drive shaft front end region and the one or more spring arms are seated in a position located behind the inner first shoulder, and the spring is rearwardly stayed on the rod against a bushing affixed to the rod, the spring pretensioning the rod toward the rear due to an axial staying of the spring arms on the inner first shoulder of the drive shaft.

2. Motor element according to claim 1, wherein the inner first shoulder is formed by an annular groove.

3. Motor element according to claim 1, wherein a plurality of spring arms are provided and arranged so that the spring arms are distributed over a periphery of a guide bushing.

4. Motor element according to claim 1, wherein each of the one or more spring arms includes a front end which, in a relaxed state, takes up a radial measure with regard to a longitudinal central axis of the hollow drive shaft that is greater than a radial measure of a receiving hole of the hollow drive shaft that is cylindrical over an entire length of the hollow drive shaft.

* * * * *